(12) United States Patent
Blaschuk et al.

(10) Patent No.: US 6,706,685 B1
(45) Date of Patent: Mar. 16, 2004

(54) COMPOUNDS AND METHODS FOR STIMULATING β-CATENIN MEDIATED GENE EXPRESSION AND DIFFERENTIATION

(75) Inventors: Orest W. Blaschuk, Westmount (CA); Stephen Byers, District of Columbia, DC (US); Barbara J. Gour, Kemptville (CA)

(73) Assignee: Adherex Technologies Inc., Ottawa (CA)

( * ) Notice: Subject to any disclaimer, the term of this patent is extended or adjusted under 35 U.S.C. 154(b) by 0 days.

(21) Appl. No.: 09/545,433

(22) Filed: Apr. 5, 2000

Related U.S. Application Data

(63) Continuation-in-part of application No. 09/288,373, filed on Apr. 5, 1999, now abandoned.

(51) Int. Cl.[7] .................. A61K 38/16; A61K 38/00; A61K 38/04; A01N 37/18

(52) U.S. Cl. .................. 514/7; 514/2; 530/326; 530/327; 530/328

(58) Field of Search .................. 514/7, 2, 13, 14, 514/15; 530/326, 327, 328; 424/184.1

(56) References Cited

U.S. PATENT DOCUMENTS

| | | | |
|---|---|---|---|
| 5,631,237 A | 5/1997 | Dzau et al. | 514/44 |
| 5,652,122 A | 7/1997 | Frankel et al. | 435/69.7 |

FOREIGN PATENT DOCUMENTS

| | | |
|---|---|---|
| WO | WO 98/45319 | 4/1997 |
| WO | WO 98/42296 | 10/1998 |
| WO | WO 99/00138 | 1/1999 |
| WO | WO 99/42481 | 8/1999 |

OTHER PUBLICATIONS

Yanin Bidault, "The next generation of bioinformatics software: Examining proteins on the desktop computer", American Biotechnology Laboratory, p. 12, Jan. 2002.*

Huber et al., Nuclear localization of b–catenin by interaction with transcription factor LEF–1, Mechanisms of Development (1996) 59:3–10.*

Remington, J. P. Remington's Pharmaceutical Sciences. PA, Mack Publ. Co., 1990 p. 1692.*

Aberle et al., "β–catenin is a target for the ubiquitin–proteasome pathway," *The EMBO Journal* 16(13):3797–3804, 1997.

Easwaran et al., "The Ubiquitin/Proteosome Pathway And Apc Regulation of Beta–Catenin/Lef Signaling," *Mol. Biol. Cell* 9:248a, Abstract No. 1440, 1998.

Gat et al., "De Novo Hair Follicle Morphogenesis and Hair Tumors in Mice Expressing a Truncated β–Catenin in Skin," *Cell* 95:605–614, 1998.

Hall et al., "Inhibition of FGF–stimulated phosphatidylinositol hydrolysis and neurite outgrowth by a cell–membrane permeable phosphopeptide," *Current Biology* 6(5):580–587, 1996.

Longer, Mark A., "Sustained–Release Drug Delivery Systems," Remington's Pharmaceutical Sciences, 18th Ed., Chapter 91, pp. 1676–1693, 1990.

(List continued on next page.)

*Primary Examiner*—Christopher S. F. Low
*Assistant Examiner*—Rita Mitra
(74) *Attorney, Agent, or Firm*—SEED Intellectual Property Law Group PLLC

(57) ABSTRACT

Modulating agents for inhibiting degradation of cytoplasmic β-catenin are provided. The modulating agents comprise one or more of: (1) the peptide sequence SYLDS(PO$_4$)GIHS(PO$_4$)G (SEQ ID NO:1) or (2) a peptide analogue or peptidomimetic thereof. Methods for using such modulating agents for stimulating β-catenin mediated gene expression and cellular differentiation are provided.

11 Claims, 2 Drawing Sheets

OTHER PUBLICATIONS

Mims et al., "A Nonexchangeable Apolipoprotein E Peptide That Mediates Binding to the Low Density Lipoprotein Receptor," *The Journal of Biological Chemistry* 269(32):20539–20547, 1994.

Oro and Scott, "Splitting Hairs: Dissecting Roles of Signaling Systems in Epidermal Development," *Cell* 95:575–578, 1998.

Oxford et al., "Serine Phosphorylation–regulated Ubiquitination and Degradation of β–Catenin," *The Journal Of Biological Chemistry* 272(40):24735–24738, 1997.

Salomon et al., "Regulation of β–Catenin Levels and Localization by Overexpression of Plakoglobin and Inhhibition of the Ubiquitin–Proteasome System," *The Journal of Cell Biology* 139(5):1325–1335, 1997.

Willert and Nusse, "β–catenin: a key mediator of Wnt signaling," *Current Opinion in Genetics and Development* 8:95–102, 1998.

Zhang et al., "Destabilization of β–catenin by mutations in presenilin–1 potentiates neuronal apoptosis," *Nature* 395:698–702, 1998.

* cited by examiner

| | |
|---|---|
| Human | MATQADLMELDMAMEPDRKAAVSHWQQQSYLDSGIHSGATTTAPSLSGKGNPEEEDVDTSQVLYEWEQGFSQSFTQEQVA |
| Chicken | MATQADLMELDMAMEPDRKAAVSHWQQQSYLDSGIHSGATTTAPSLSGKGNPEEEDVDTTQVLYEWEQGFSQSFTQEQVA |
| Frog | MATQADLMELDMAMEPDRKAAVSHWQQQSYLDSGIHSGATTTAPSLSGKGNPEDEDVDTNQVLYEWEQGFSQSFTQDQVA |
| Mouse | MATQADLMELDMAMEPDRKAAVSHWQQQSYLDSGIHSGATTTAPSLSGKGNPEEEDVDTSQVLYEWEQGFSQSFTQEQVA |
| Zebrafish | MATQSDLMELEMAMDPDRKAAVSHWQQQSYLDSGIHSGATTTAPSLSGKGNPEDDDVDN-QVLYEWEQGFNQSFNQEQVA |
| | |
| Consensus | MATQaDLMELdMAMePDRKAAVSHWQQQSYLDSGIHSGATTTAPSLSGKGNPEeeDVDtxQVLYEWEQGFsQSFtQeQVA |

FIG. 1

SEQUENCE LISTING

```
<160> NUMBER OF SEQ ID NOS:  15

<210> SEQ ID NO 1
<211> LENGTH: 10
<212> TYPE: PRT
<213> ORGANISM: Artificial Sequence
<220> FEATURE:
<223> OTHER INFORMATION: Modulating agent derived from beta-catenin
<221> NAME/KEY: PHOSPHORYLATION
<222> LOCATION: (5)...(5)
<221> NAME/KEY: PHOSPHORYLATION
<222> LOCATION: (9)...(9)

<400> SEQUENCE: 1

Ser Tyr Leu Asp Ser Gly Ile His Ser Gly
1               5                   10

<210> SEQ ID NO 2
<211> LENGTH: 80
<212> TYPE: PRT
<213> ORGANISM: Homo sapien

<400> SEQUENCE: 2

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

<210> SEQ ID NO 3
<211> LENGTH: 80
<212> TYPE: PRT
<213> ORGANISM: Gallus gallus

<400> SEQUENCE: 3

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Thr Gln Val Leu Tyr
    50                  55                  60

Glu Trp Glu Gln Gly Phe Ser Gln Ser Phe Thr Gln Glu Gln Val Ala
65                  70                  75                  80
```

```
<210> SEQ ID NO 4
<211> LENGTH: 80
<212> TYPE: PRT
<213> ORGANISM: Xenopus leavis

<400> SEQUENCE: 4

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Asp Glu Asp Val Asp Thr Asn Gln Val Leu Tyr
    50                  55                  60

Glu Trp Glu Gln Gly Phe Ser Gln Ser Phe Thr Gln Asp Gln Val Ala
65                  70                  75                  80

<210> SEQ ID NO 5
<211> LENGTH: 80
<212> TYPE: PRT
<213> ORGANISM: Mus musculus

<400> SEQUENCE: 5

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

<210> SEQ ID NO 6
<211> LENGTH: 79
<212> TYPE: PRT
<213> ORGANISM: Donio rerio

<400> SEQUENCE: 6

Met Ala Thr Gln Ser Asp Leu Met Glu Leu Glu Met Ala Met Asp Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Asp Asp Val Asp Asn Gln Val Leu Tyr Glu
    50                  55                  60

Trp Glu Gln Gly Phe Asn Gln Ser Phe Asn Gln Glu Gln Val Ala
65                  70                  75

<210> SEQ ID NO 7
<211> LENGTH: 80
<212> TYPE: PRT
<213> ORGANISM: Consensus sequence of Homo, Gallus, Xenopus, Mus
<220> FEATURE:
<221> NAME/KEY: VARIANT
<222> LOCATION: (1)...(80)
<223> OTHER INFORMATION: Xaa = Any Amino Acid
```

```
<400> SEQUENCE: 7

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Xaa Gln Val Leu Tyr
    50                  55                  60

Glu Trp Glu Gln Gly Phe Ser Gln Ser Phe Thr Gln Glu Gln Val Ala
65                  70                  75                  80

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide to demonstrate cyclization
<221> NAME/KEY: ACETYLATION
<222> LOCATION: (1)...(1)
<221> NAME/KEY: METHYLATION
<222> LOCATION: (4)...(4)

<400> SEQUENCE: 8

Trp Gly Gly Trp
1

<210> SEQ ID NO 9
<211> LENGTH: 16
<212> TYPE: PRT
<213> ORGANISM: Drosophila melanogaster

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 16
<212> TYPE: PRT
<213> ORGANISM: Drosophila melanogaster

<400> SEQUENCE: 10

Arg Gln Ile Lys Ile Trp Pro Gln Asn Arg Arg Asn Lys Trp Lys Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Analogue of Drosphilia Antennapedia protein

<400> SEQUENCE: 11

Lys Lys Trp Lys Lys Trp Trp Lys Lys Trp Trp Lys Lys Trp Lys Lys
1               5                   10                  15

<210> SEQ ID NO 12
<211> LENGTH: 26
<212> TYPE: PRT
<213> ORGANISM: Artificial Sequence
<220> FEATURE:
<223> OTHER INFORMATION: Beta-catenin modulating agent covalently linked
      to the Antennapedia internalization sequence
<221> NAME/KEY: PHOSPHORYLATION
<222> LOCATION: (5)...(5)
```

```
<221> NAME/KEY: PHOSPHORYLATION
<222> LOCATION: (9)...(9)

<400> SEQUENCE: 12

Ser Tyr Leu Asp Ser Gly Ile His Ser Gly Arg Gln Ile Lys Ile Trp
1               5                   10                  15

Phe Gln Asn Arg Arg Asn Lys Trp Lys Lys
            20                  25

<210> SEQ ID NO 13
<211> LENGTH: 18
<212> TYPE: PRT
<213> ORGANISM: Artificial Sequence
<220> FEATURE:
<223> OTHER INFORMATION: Alph-helix amphipathic model peptide

<400> SEQUENCE: 13

Lys Leu Ala Leu Lys Leu Ala Leu Lys Leu Ala Lys Ala Ala Leu Lys
1               5                   10                  15

Leu Ala

<210> SEQ ID NO 14
<211> LENGTH: 11
<212> TYPE: PRT
<213> ORGANISM: Human immunodeficiency virus

<400> SEQUENCE: 14

Tyr Gly Arg Lys Lys Arg Arg Gln Arg Arg Arg
1               5                   10

<210> SEQ ID NO 15
<211> LENGTH: 22
<212> TYPE: PRT
<213> ORGANISM: Artificial Sequence
<220> FEATURE:
<223> OTHER INFORMATION: Beta-catenin modulating agent linked with TAT
      protein transduction domain
<221> NAME/KEY: PHOSPHORYLATION
<222> LOCATION: (17)...(17)
<221> NAME/KEY: PHOSPHORYLATION
<222> LOCATION: (21)...(21)

<400> SEQUENCE: 15

Tyr Gly Arg Lys Lys Arg Arg Gln Arg Arg Arg Gly Ser Tyr Leu Asp
1               5                   10                  15

Ser Gly Ile His Ser Gly
            20
```

COMPOUNDS AND METHODS FOR STIMULATING β-CATENIN MEDIATED GENE EXPRESSION AND DIFFERENTIATION

CROSS-REFERENCE TO RELATED APPLICATIONS

This application is a continuation-in-part of U.S. Ser. No. 09/288,373, filed Apr. 5, 1999 now abandoned.

TECHNICAL FIELD

The present invention relates generally to compounds and methods for use in stimulating β-catenin mediated gene expression and cellular differentiation. The invention is more specifically related to modulating agents capable of increasing the level of free β-catenin in a cell cytoplasm, and to therapeutic methods employing such agents.

BACKGROUND OF THE INVENTION

β-catenin is a cytoplasmic protein that is critical for classical cadherin-mediated intercellular adhesion. Inside the cell, a β-catenin/(α-catenin complex interacts with the second cytoplasmic domain (CP2) of the classical cadherins. In the absence of this β-catenin/α-catenin complex, the classical cadherins cannot promote cell adhesion (see Wheelock et al., *Current Topics in Membranes* 43:169–185, 1996).

In addition to its role in cell adhesion, β-catenin also appears to be a key component of certain cellular signaling pathways, leading to activation of gene expression and a variety of developmental processes, such as differentiation. In particular, β-catenin functions in Wnt-mediated signaling, associating with LEF-1/TCF DNA binding proteins to form a transcription factor (see FIG. 2). The level of signal transduction appears to correlate with the level of free β-catenin in the cytoplasm of the cell (see Willert and Nusse, *Genetics and Development* 8:95–102, 1998). Glycogen synthase kinase 3β(GSK-3β) and adenomatous polyposis coli tumor suppressor protein (APC) interact with cytoplasmic β-catenin and facilitate its degradation via the ubiquitin/proteosome pathway (see FIG. 2).

Wnt-mediated signaling is involved in a variety of developmental processes, including cellular differentiation. For example, skin cells expressing a stabilized form of β-catenin display increased hair growth (Gat et al., *Cell* 95:605–614, 1998; Ono et al., *Cell* 95:575–578, 1998). Thus, therapies based on increasing the level of free β-catenin in the cytoplasm have potential for stimulating Wnt-mediated signal transduction, resulting in differentiation and, in certain instances, enhanced hair growth. However, there are presently no available therapies for modulating Wnt-mediated signaling.

Accordingly, there is a need in the art for improved methods for inducing Wnt-mediated signal transduction and cellular differentiation. The present invention fulfills this need and further provides other related advantages.

SUMMARY OF THE INVENTION

The present invention provides methods for stimulating β-catenin mediated gene transcription and cellular differentiation. Within certain aspects, the present invention provides modulating agents capable of increasing the level of free β-catenin in a cell. In one such aspect, the modulating agent comprises an internalization moiety and one or more of: (a) the amino acid sequence SYLDS(PO$_4$)GIHS(PO$_4$)G (SEQ ID NO:1) or (b) a peptide analogue or peptidomimetic of the amino acid sequence SYLDS(PO$_4$)GIHS(PO$_4$)G (SEQ ID NO: 1). The internalization moiety may comprise, within certain embodiments, an internalization sequence covalently linked to the modulating agent, a liposome that encapsulates the modulating agent or an antibody or ligand that binds to a cell surface receptor. Within further embodiments, any of the above modulating agents may be linked to a targeting agent and/or a drug.

Within other aspects, the present invention provides pharmaceutical compositions comprising a modulating agent as described above, in combination with a pharmaceutically acceptable carrier.

The present invention further provides, within other aspects, methods for increasing the level of β-catenin in a cell, comprising contacting a cell with a modulating agent as described above.

Within further related aspects, the present invention provides methods for stimulating the activation of β-catenin mediated gene transcription in a cell, comprising contacting a cell with a modulating agent as described above.

Within further related aspects, the present invention provides methods for stimulating differentiation of a cell, comprising contacting a cell with a modulating agent as described above. In certain embodiments, the cell is a skin cell, such as a keratinocyte.

In other aspects, methods are provided for stimulating hair growth or reducing hair loss on a mammal, comprising administering to a mammal a modulating agent as described above. Such administration may be topical, and the skin cells may be present, for example, on the scalp or within the ear of the mammal.

The present invention further provides, within other aspects, methods for stimulating exfoliation of skin on a mammal, comprising administering to a mammal a modulating agent as described above.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 1 presents an alignment of representative amino terminal regions of β-catenin from human, chicken, frog, mouse and zebrafish (SEQ ID NOs:2 to 6 respectively). Sequences were aligned using a Clustal W protein sequence alignment. Amino acids are represented by their IUPAC amino acid codes, where X is any amino acid and "-" represents a gap. The consensus sequence (60% or better) is shown in italics (SEQ ID NO:7), and amino acid capitalized within the consensus sequence represent identity. The β-catenin phosphorylation region is shown in bold.

DETAILED DESCRIPTION OF THE INVENTION

Figure 2:
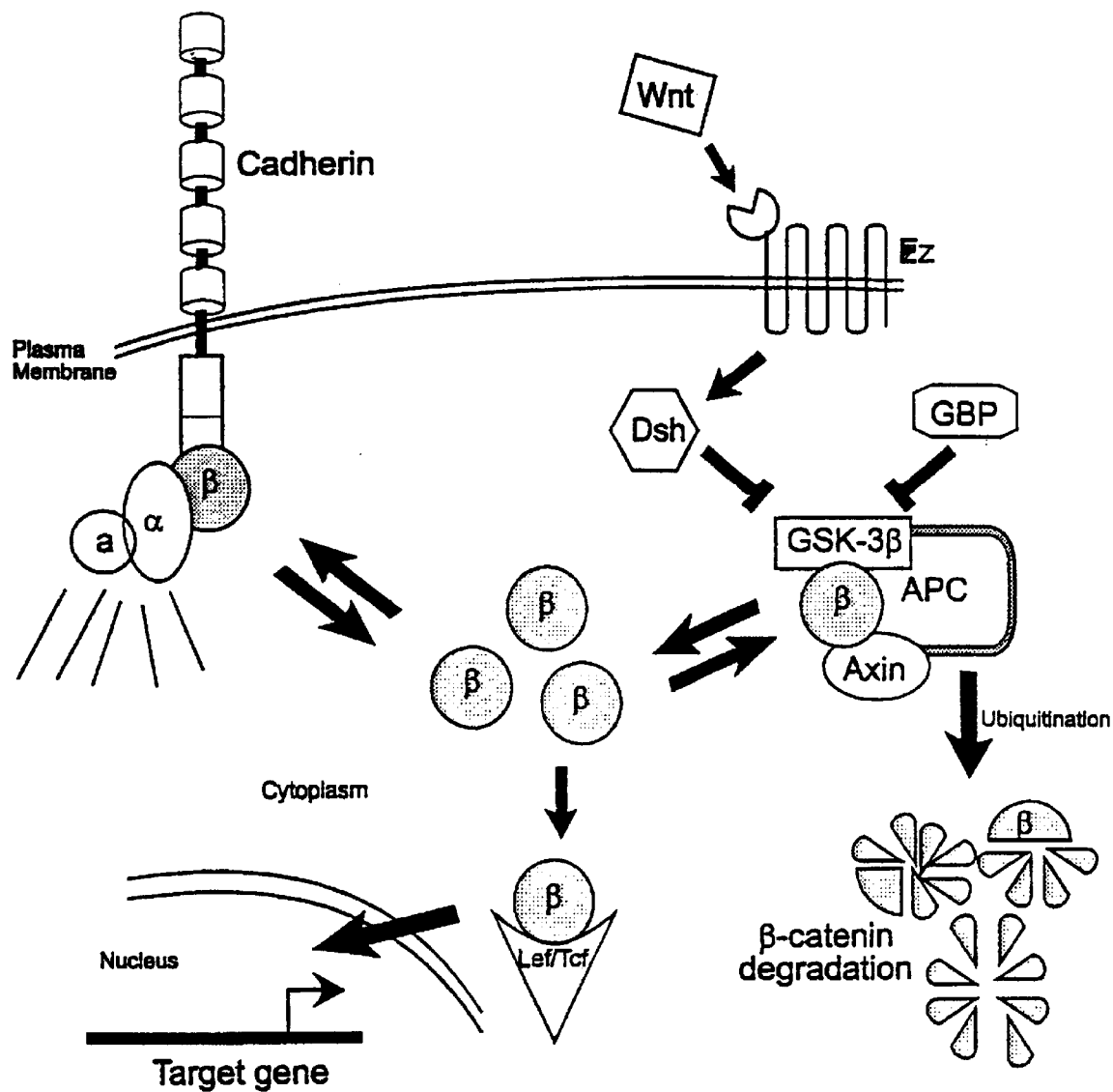
FIG. 2 is a schematic diagram of β-catenin cellular functions. To enhance intercellular adhesion, β-catenin (β) forms a complex with α-catenin (α), alpha-actinin (a) and a cell surface cadherin. In the pathway starting with Wnt, the inactivation of glycogen synthase kinase 3β(GSK-3β) leads to stabilization and accumulation of cytoplasmic β-catenin, which interacts with the Lef/Tcf transcription factor, leading to target gene activation. In the absence of Wnt signal, GSK-3β binds to the adenomatous polyposis coli tumor suppressor protein (APC)/β-catenin complex, leading to ubiquitination and degradation.

As noted above, the present invention provides methods for stimulating β-catenin mediated gene transcription and cellular differentiation. The present invention is based, in part, on the discovery that agents comprising the sequence SYLDS(PO$_4$)GIHS(PO$_4$)G (SEQ ID NO:1) and an internalization moiety are capable of entering a cell and inhibiting the degradation of cytoplasmic β-catenin. The resulting accumulation of β-catenin in the cytoplasm functions as a transcriptional activator, leading to responses such as cellular differentiation. Modulating agents that comprise the sequence SYLDS(PO$_4$)GIHS(PO$_4$)G (SEQ ID NO:1) as provided herein may be used to stimulate β-catenin mediated gene transcription within a variety of contexts. For example, such agents may be used to stimulate hair growth or to stimulate exfoliation of skin.

Modulating Agents

As noted above, the term "modulating agent," as used herein, refers to a molecule comprising one or more of (1) the peptide sequence SYLDS(PO$_4$)GIHS(PO$_4$)G (SEQ ID NO:1) or (2) a peptide analogue or peptidomimetic thereof. The above peptide sequence is derived from β-catenin (residues 29–38), and the serine residues at positions 33 and 37 are phosphorylated, as indicated by the (PO$_4$) in the peptide sequence (i.e., the —OH present within the serine side chains of the designated residues is replaced by —O—PO$_3$). A modulating agent is further capable of inhibiting degradation of cytoplasmic β-catenin, as described herein. Within preferred embodiments, a modulating agent further comprises an internalization moiety, which is associated (covalently or noncovalently) with one or more of the above components.

Peptide agents as described herein may, but need not, contain additional amino acid residues from β-catenin. Such additional residues may flank the SYLDS(PO$_4$)GIHS(PO$_4$)G (SEQ ID NO:1) sequence in a native β-catenin molecule (i.e., may be adjacent to that sequence in a native β-catenin molecule). Flanking sequences for β-catenin of a variety of organisms are shown in SEQ ID NOs:2 to 7, and FIG. 1. Flanking residue(s) may be present on the N-terminal and/or C-terminal side of the above peptide sequence, preferably on both sides. A modulating agent may consist entirely of a β-catenin sequence, or may additionally comprise further peptide and/or non-peptide regions, such as regions that facilitate cyclization, purification or other manipulation, and/or residues having a targeting or other function. Agents comprising derivatives of SYLDS(PO$_4$)GIHS(PO$_4$)G (SEQ ID NO:1) having one or more side chain modifications are also contemplated. Modulating agents may further be associated (covalently or noncovalently) with a targeting agent, drug, solid support and/or detectable marker.

Modulating agents, or peptide portions thereof, may be linear or cyclic peptides. A "linear" peptide is a peptide or salt thereof that does not contain an intramolecular covalent bond between two non-adjacent residues. Within preferred embodiments, linear peptide modulating agents typically comprise from 10 to about 20 amino acid residues derived from β-catenin, preferably from 10 to 16 amino acid residues derived from β-catenin.

The term "cyclic peptide," as used herein, refers to a peptide or salt thereof that comprises an intramolecular covalent bond between two non-adjacent residues, forming a cyclic peptide ring that comprises the SYLDS(PO$_4$)GIHS(PO$_4$)G (SEQ ID NO:1) sequence. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide bonds; amide bonds between terminal functional groups, between residue side chains or between one terminal functional groups and one residue side chain; thioether bonds and δ$_1$,δ$_1$-ditryptophan or a derivative thereof. Preferred cyclic peptide modulating agents generally contain 10 to 15 residues within the cyclic peptide ring.

As noted above, modulating agents may be polypeptides or salts thereof, containing only amino acid residues linked by peptide bonds, or may additionally comprise non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations shown in Table 1.

TABLE 1

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g, acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

As noted above, a modulating agent may comprise a peptide analogue or a non-peptide peptidomimetic of a SYLDS(PO$_4$)GIHS(PO$_4$)G (SEQ ID NO:1) sequence, provided that the analogue or peptidomimetic retains the ability to stimulate a β-catenin mediated response. In general, a peptide analogue may contain conservative substitutions such that the ability to stimulate a β-catenin mediated response is not substantially diminished. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of a peptide analogue is the ability to inhibit degradation of cytosolic β-catenin. Such an ability may be evaluated using the representative assays provided herein.

A peptidomimetic is a non-peptide compound that is structurally similar to the peptide sequence SYLDS(PO$_4$)GIHS(PO$_4$)G (SEQ ID NO:1), such that the peptidomimetic retains the ability to stimulate a β-catenin mediated response, as described below. Peptidomimetics are organic compounds that mimic the three-dimensional shape of the peptide sequence SYLDS(PO$_4$)GIHS(PO$_4$)G (SEQ ID NO:1). Peptidomimetics may be designed based on techniques that evaluate the three dimensional shape, such as nuclear magnetic resonance (NMR) and computational techniques. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the peptide sequence SYLDS(PO$_4$)GIHS(PO$_4$)G (SEQ ID NO:1). Once the lowest energy conformation is known, the three-dimensional shape to be mimicked is known. It should be understood that, within embodiments described herein, an analogue or peptidomimetic may be substituted for the sequence SYLDS(PO$_4$)GIHS(PO$_4$)G (SEQ ID NO:1).

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for ac-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Within preferred synthesis methods, a phosphorylated peptide modulating agent such as N—Ac-SYLDS(PO$_4$)GIHS(PO$_4$)G—NH$_2$ (SEQ ID NO:1) may be prepared using solid phase peptide synthesis techniques that allow selective phosphorylation of hydroxy-containing residues of the peptide. Such a peptide may be assembled using Boc or Fmoc-amino acid-OPfp (pentafluorophenyl) and amino-acid-ODhbt (3,4-Dihydro-3-hydroxy-4-oxo-1,2,3-benztriazine) activated esters. Their high reactivity and selectivity towards amino groups allows the introduction of serine, threonine, and tyrosine without side-chain protection. This strategy allows the incorporation of O-unprotected serine residues in the peptide chain at specific positions for later phosphorylation and incorporation of protected serine residues when no phosphorylation is needed. Phosphorylation of the unprotected amino acid side-chain hydroxyl groups may be carried out on the solid support after the assembly of the linear peptide is complete. Alternatively, the peptide is prepared by phosphorylating the serine residues of cleaved, purified peptides or using appropriately protected, phosphorylated serine residues that can be incorporated into the peptide like any regular amino acid.

For protection, t-Butyloxycarbonyl (Boc) may be used as the protecting group used for the histidine side-chain, and the t-butyl ester may be used to protect the side chains of aspartic acid, tyrosine and the serine residues which are not to be phosphorylated. The appropriate pentafluorophenyl ester of the unprotected serine may be made in situ from Fmoc-serine and pentaflurophenol with DIC in DMF. The N-terminal amino acid can be protected with Boc when the free amine is required on the N-terminus or with an acetyl group if the N-acetylated peptide is required after cleavage. Upon completion of the peptide chain assembly, the free hydroxyl groups of the serine residues may be phosphorylated with dibenzylphosphochloridate. Cleavage of protecting groups may be carried out by suspending the resin in a mixture of TFA, phenol and anisole.

Another method to prepare such peptides includes phosphorylating the serine residues of cleaved, purified peptides while other amino acids are protected. For example, a linear peptide can be assembled in solution, using Boc amino acids as activated esters (hydroxybenztriazole ester). The Boc group can be removed with saturated HCl in ether. The side-chain of the serine to be phosphorylated can be protected with a benzyl group and then introduced into the sequence. In order to phosphorylate the peptide, the serine side chain may be deprotected by hydrogenolysis using palladium black in methanol and acetic acid, followed by phosphitylation using diethylaminobenzylphosphoramidite in the presence of tetrazole. The resulting phosphite is immediately oxidized with excess tert-butylhydroperoxide. Final deprotection is achieved by acidolysis with trifluromethanesulfonic acid in trifluoroacetic acid to remove all protecting groups from the peptide.

Yet another method for preparation of phosphorylated peptides involves the use of appropriately protected phosphorylated serine residues that can be incorporated into the peptide, as would be a regular amino acid. A protected phosphoester serine that is stable under the conditions of solid phase peptide synthesis has to be prepared. This can be done by different phosphorylating agents such as aryl or alkyl phosphorochloridate, phosphorochloriditite, and N,N-dialkyl phosphoramidite. The last two methods require subsequent in situ oxidation of phosphite triester intermediates into phosphate triesters. The choice of phosphate protecting groups is crucial for the synthesis of phosphopeptides. Phenyl and benzyl groups are widely used and both are easily removed by catalytic hydrogenation. Both liquid and solid-phase Boc methodologies can be utilized to prepare the phosphopeptide using Merrifield resin. These may require repetitive treatments with TFA to remove Boc protecting groups and with HF for the final cleavage, followed by catalytic hydrogenation to remove phosphate protecting groups.

It will be apparent to those of ordinary skill in the art that modifications may be made to the synthesis procedures described herein, provided that deprotection and coupling reactions go to completion and the side-chain blocking groups are stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation may be accomplished using an appropriate resin such as methylbenzhydrylamine resin using the Boc technology.

Following synthesis of a linear peptide, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, $\beta,\beta$-dimethyl cysteine (penicillamine or Pen), $\beta,\beta$-tetramethylene cysteine (Tmc), $\beta,\beta$-pentamethylene cysteine (Pmc), $\beta$-mercaptopropionic acid (Mpr), $\beta,\beta$-pentamethylene-$\beta$-mercaptopropionic acid (Pmp), 2-mercaptobenzene, 2-mercaptoaniline and 2-mercaptoproline.

Within another embodiment, cyclization may be achieved by amide bond formation. For example, a peptide bond may be formed between terminal functional groups (i.e., the amino and carboxy ternmini of a linear peptide prior to cyclization), with or without an N-terminal acetyl group and/or a C-terminal amide. Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), $\alpha$-amino adipic acid, m-aminomethylbenzoic acid, $\alpha,\beta$-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "lactive esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized (α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Cyclization may also be achieved using $\delta_1,\delta_1$-ditryptophan.

For longer peptide modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g, hybridoma, CHO, myeloma). The DNA sequences expressed in this manner may encode portions of an endogenous β-catenin and/or other sequences. Endogenous β-catenin sequences may be prepared based on known cDNA or genomic sequences (see Wheelock et al., *Current Topics in Membranes* 43:169–185, 1996), which may be isolated by screening an appropriate library with probes designed based on such known sequences. Screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous β-catenin. To generate a nucleic acid molecule encoding a desired modulating agent, an endogenous β-catenin sequence may be modified using well known techniques. Alternatively, portions of the desired nucleic acid sequences may be synthesized using well known techniques, and then ligated together to form a sequence encoding the modulating agent.

Within preferred embodiments, a modulating agent comprises an internalization moiety. An internalization moiety is any moiety (such as a compound, liposome or particle) that can be used to improve the ability of an agent to penetrate the lipid bilayer of the cellular plasma membrane, thus enabling the agent to readily enter the cytoplasm. As used herein, the term "associated with" refers to covalent attachment or a non-covalent interaction mediated by, for example, ionic bonds, hydrogen bonds, van der waals forces and/or hydrophobic interactions, such that the internalization moiety and modulating agent remain in close proximity under physiological conditions.

Within certain embodiments, an internalization moiety is a peptide internalization sequence. An internalization sequence may be any sequence (generally a peptide sequence) that is capable of facilitating entry of the modulating agent into the cytosol of a living cell. One suitable internalization sequence is a 16 amino acid peptide derived from the third helix of the Antennapedia protein, and having the sequence RQIKIWFQNRRMKWKK (SEQ ID NO:9; see Prochiantz, *Curr. Op. Neurobiol.* 6:629–34, 1996) or RQIKIWPQNRRNKWKK (SEQ ID NO:10). Analogues of this sequence (i.e., sequences having at least 25% sequence identity, such that the ability to facilitate entry into the cytosol is not diminished) may also be employed. One such analogue is KKWKKWWKKWWKKWKK (SEQ ID NO:11). One preferred modulating agent that comprises a covalently linked Antennapedia internalization sequence has the sequence SYLDS(PO$_4$)GIHS(PO$_4$)GRQIKIWFQNRRNKWKK (SEQ ID NO: 12).

Alternatively, an internalization sequence may be unrelated to the Antennapedia sequence. Any sequence that facilitates entry to the cell, via a cell surface receptor or other means, may be employed. Protein-derived helical peptide sequences that may be used as internalization sequences include, but are not limited to, KLALKLALKLA-KAALKLA (SEQ ID NO:13; see Oehlke et al., *Biochim. Biophys. Acta* 1414:127–139, 1998, and references cited therein). Other internalization sequences include the 11 amino acid TAT protein transduction domain YGRKKRRQRRR (SEQ ID NO:14; see Nagahara et al., *Nature Medicine* 4:1449–1452, 1998) and the transduction domain of HSV VP22 (see Elliot and O'Hare, *Cell* 88:223–244, 1997). One preferred modulating agent comprising the TAT protein transduction domain is YGRKKRRQRRRGSYLDS(PO$_4$)GIHS(PO$_4$)G (SEQ ID NO: 15).

In general, the ability of a sequence to facilitate entry into the cytosol may be evaluated in any of a variety of ways. For example, a candidate internalization sequence may be covalently linked to the sequence SYLDS(PO$_4$)GIHS(PO$_4$)G (SEQ ID NO:1) and contacted with cells. The ability of such a construct to stimulate a β-catenin mediated response, as described herein, may then be assessed.

Alternatively, the ability of a candidate internalization sequence to cross the plasma membrane may be assessed directly using any assay known in the art. Within such any assay, an internalization sequence should result in a response that is statistically greater than that observed in the absence of internalization sequence. Preferably, an internalization sequence incorporated into a modulating agent results in a response that is comparable to, or greater than, that observed for the modulating agent comprising an internalization sequence derived from TAT, as described above.

An internalization sequence may be covalently linked to the remainder of a modulating agent. Such linkage may be generated using any of a variety of means well known in the art, either directly or by way of a spacer. In general, spacers may be amino acid residues (e.g., amino hexanoic acid) or peptides, or may be other bi- or multi-functional compounds that can be covalently linked to at least two peptide sequences. Covalent linkage may be achieved via direct condensation or other well known techniques.

Other internalization moieties may be covalently or non-covalently linked to the remainder of the modulating agent. For example, the β-catenin derived portion of the modulating agent may be encapsulated by the liposome (i.e., an artificial membrane vesicle), using well known technology. Other internalization moieties include, but are not limited to, antibodies and ligands that bind to cell surface receptors. Alternatively, a polynucleotide encoding a modulating agent may be incorporated into an appropriate viral vector, such that the modulating agent is generated within the target cell. Various particle-mediated delivery systems are also available, and their use is well known to those of ordinary skill in the art.

Evaluation of Modulating Agent Activity

As noted above, modulating agents are capable of inhibiting degradation of cytoplasmic β-catenin. This ability may generally be evaluated using any suitable assay known to those of ordinary skill in the art. For example, an immunoprecipitation assay as described herein may be employed. Within such an assay, decreased degradation of β-catenin is measured by assessing the ability of an antibody directed against β-catenin to immunoprecipitate full length β-catenin from cell lysates in the presence and absence of the modulating agent. For example, mammalian cells that express β-catenin (see Pishvaian et al., *Cancer Res.* 59:947–952, 1999) may be homogenized in the presence and absence of modulating agent. An antibody directed against β-catenin is used to immunoprecipitate β-catenin from the homogenate, and a Western blot analysis of immunoprecipitated protein is used to evaluate the level of full length β-catenin. In general, a modulating agent should increase the level of cytoplasmic β-catenin by at least 50%.

Alternatively, or in addition, the effect of a modulating agent on any of a variety of β-catenin-mediated processes may be evaluated. The effect of a modulating agent on β-catenin mediated gene transcription may be determined using any appropriate assay, such as the keratinocyte differentiation assay provided herein. Briefly, keratinocytes may be treated with a candidate modulating agent (e.g., 1 mg/ml for 48 hours). Treated and untreated cells are then photographed. At a concentration of 1 mg/ml, a modulating agent should detectably induce the formation of terminally differentiated cells known as squams, which may be identified based on detachment from the substratum, and morphological alterations that are well known to those of ordinary skill in the art.

Other suitable assays are those designed to detect changes in hair growth. Such assays may be performed using plucked hair or hair follicles cultured in vitro. Such assays are described, for example, within U.S. Pat. Nos. 5,527,772 and 5,739,111. For assays using hair, the effect of a modulating agent may be determined based on DNA content in the hair. Increased DNA content should be observed in hair cultured for 48 hours in the presence of 1 mg/ml modulating agent, relative to hair cultured in the absence of modulating agent. In vivo assays may be performed, for example, by application of a modulating agent to shaved skin on a mouse, in which a modulating agent results in increased hair density and/or hair length.

Modulating Agent Modification and Formulations

A modulating agent as described herein may, but need not, be linked to one or more additional molecules. Although modulating agents as described herein may preferentially bind to specific tissues or cells, and thus may be sufficient to target a desired site in vivo, it may be beneficial for certain applications to include an additional targeting agent. Accordingly, a targeting agent may be associated with a modulating agent to facilitate targeting to one or more specific tissues. As used herein, a "targeting agent" may be any substance (such as a compound or cell) that, when associated with a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[V] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 µg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of use

In general, the modulating agents and compositions described herein may be used for stimulating β-catenin mediated gene transcription. Such stimulation may be performed in vitro and/or in vivo, preferably in a mammal such as a human. Within each of the methods described herein, one or more modulating agents may generally be administered alone, or within a pharmaceutical composition. In each specific method described herein, as noted above, a targeting agent may be employed to increase the local concentration of modulating agent at the target site.

βcatenin mediated gene transcription may be stimulated in any of a variety of contexts. As used herein, the phrase "β-catenin mediated gene transcription" refers to the transcription of any gene that increases in the presence of increased levels of cytosolic β-catenin. Such genes include, but are not limited to, genes that are activated by the Wnt-mediated signaling pathway, such as c-myc (see He et al., *Science* 281:1509–12, 1998).

Within certain aspects, the present invention provides methods for increasing the level of cytoplasmic β-catenin in a cell. Such methods comprise the step of contacting a cell with a modulating agent as described herein. The step of contacting may be performed using any method that is suitable for the particular cell type. In vitro, for example, contacting may be achieved by adding modulating agent to the growth medium. In vivo, contact may be achieved by administration, as described herein. For administration to skin cells, topical administration is generally preferred. Contact is performed using an amount of agent and for a sufficient duration to result in a detectable increase in the level of β-catenin in the cell. Such an increase may be detected directly (e.g., using immunohistochemical methods), or indirectly, based on a detection of cellular differentiation, as described herein.

Contact with a modulating agent as described above further results in enhanced activation of β-catenin mediated gene transcription in the cell. Such activation may be readily detected using any standard method for detecting changes in transcription, such as hybridization techniques and amplification techniques involving polymerase chain reaction (PCR). Alternatively, downstream effects of such transcription may be detected. Such downstream effects may include, but are not limited to, terminal differentiation and hair growth.

As noted above, contact of a cell with a modulating agent as described herein may stimulate terminal differentiation of the cell. Accordingly, the present invention provides methods for using a modulating agent to stimulate differentiation in a cell. Cells in which differentiation may be stimulated include, but are not limited to, skin cells, such as keratinocytes. Terminal differentiation may be detected by photographic methods, based on standard criteria that are well known in the art. For example, one sign of terminal differentiation is the loss of intermediate filament bundles.

Contact of a skin cell with a modulating agent may further stimulate hair growth. For such applications, administration is preferably achieved by direct contact with the scalp of the mammal (e.g., by topical application or cutaneous injection). Enhanced hair growth may be detected based on increased hair density and/or rate of growth.

It has been found, within the context of the present invention, that a modulating agent can induce keratinocytes to terminally differentiate into squams. Accordingly, a modulating agent may be used to cause the shedding (exfoliation) of old skin. For such uses, administration is preferably topical, with direct application to the skin of a mammal. Enhancement of exfoliation may be beneficial, for example, in plastic surgery, for improvement of photodamaged skin and for minimization of wrinkles. Such modulating agents may represent an improvement over harsh chemical exfoliants presently in use. Enhancement of exfoliation may generally be detected based on the appearance of new skin, which may be identified visually or using any of a variety of well known assays for detecting sloughing of skin cells.

A modulating agent may further be used to ameliorate hearing loss resulting from a variety of inner ear disorders, such as hyperacusis and tinnitus. Regeneration of hair cells of the inner ear, by contact with a modulating agent as described herein, may result in improvement in such ear disorders and lessened hearing loss.

Modulating agents as provided herein may also be used to inhibit the development of Alzheimer's disease. Within such methods, a modulating agent may be administered to a patient that is at risk for developing Alzheimer's disease (but without detectable symptoms), or may be administered following diagnosis of the disease, based on clinical parameters that are accepted by those skilled in the art. Modulating agents may be administered to a patient alone or in combination with other therapeutic agents. In general, a modulating agent is administered in an amount sufficient to delay the onset, slow the progression or effect an improvement in symptoms of the disease.

The following Example is offered by way of illustration and not by way of limitation.

EXAMPLE

Preparation of Representative Modulating Agents

This Example illustrates the solid phase synthesis of a representative phosphorylated peptide modulating agent.

N—Ac-SYLDS(PO$_4$)GIHS(PO$_4$)G—NH$_2$ (SEQ ID NO:1) is prepared using solid phase peptide synthesis techniques that allow selective phosphorylation of hydroxy-containing residues of the peptide. The peptide is assembled using Boc or Fmoc-amino acid-OPfp (pentafluorophenyl) and amino-acid-ODhbt (3,4-Dihydro-3-hydroxy-4-oxo-1,2,3-benztriazine) activated esters. When phosphorylating on the resin, the peptide is assembled on Rink Amide AM resin (4-(2',4'-Dimethoxyphenyl-Fmoc-aminomethyl)-phenoxyacetamidoaminomethyl, 0.65 meq/g, 1% DVB Grain size 200–400 mesh, available from CHEM-IMPEX, Wood Dale, Ill.) (0.150 g) using the Fmoc procedure. In each cycle the N-protecting Fmoc-group is removed with piperidine-DMF solution (20% v/v) 20 minutes. After washing two times with DMF, a six fold molar excess of the next Fmoc-amino acid pentafluorophenyl ester in DMF is added. After monitoring the coupling for completion, the resin is washed 2 times with DMF. Couplings are carried out over a 4–6 hour period. t-Butyloxycarbonyl (Boc) is the protecting group used for the histidine side-chain, and the t-butyl ester is used to protect the side chains of aspartic acid, tyrosine and the serine residues which are not to be phosphorylated. The appropriate pentafluorophenyl ester of the unprotected serine is made in situ from Fmoc-serine and pentaflurophenol with DIC in DMF. The N-terminal amino acid can be protected with Boc when the free amine is required on the N-terminus or with an acetyl group if the N-acetylated peptide is required after cleavage.

Upon completion of the peptide chain assembly, the free hydroxyl groups of the serine residues are phosphorylated with dibenzylphosphochloridate (1.2 M), prepared in situ from dibenzylphosphite and N-chlorosuccinimide in dry toluene. The resin (0.15 g, peptide content: 0.075 mmol for the acetylated peptide) is suspended in a dry solution containing toluene:pyridine at a ratio of 1:2 respectively (1 mL). The mixture is cooled to –40° C. and 0.3 mL of the dibenzylphosphochloridate solution is added. The reaction mixture is brought to –20° C. and stirred for 3 hours. The same procedure is repeated, and a third coupling is performed overnight at room temperature. The resin is washed once with dry pyridine, twice with dry toluene and finally with DCM. The cleavage is carried out by suspending the resin in a cleavage cocktail (consisting of TFA: phenol: anisole, (96 mL:2 g: 2 mL respectively)) and shaking for 4 hours. The resin is filtered and washed with dichloromethane. The solvent volume is reduced under vacuum (water aspirator) to approximately 2 mL and the crude product is precipitated with the addition of cold ether and lyophilized from 0.1% TFA. This cleavage procedure removes all protecting groups. Peptides can be purified on a reverse phase HPLC using a linear gradient of acetonitrile in 0.1% aqueous TFA solution.

As an alternative, phosphorylated peptides can be prepared using the commercially available Wang resin (CHEM-IMPEX, Wood Dale, Ill.) with Fmoc-protected glycine as the first amino acid (Fmoc-Gly-p-benzyloxybenzyl alcohol resin, 0.55 mmol/g). The peptide may be assembled on the solid support using Fmoc-amino-acid-ODhbt (3,4-Dihydro-3-hydroxy-4-oxo-1,2,3-benztriazine) activated esters, without side-chain protection on the serine residues which are to be phosphorylated, and with the serine side chain protected as the t-butyl ester for the serine residues which are not to be phosphorylated (N-Ac-Ser (OtBu)-Odhbt). Coupling reactions are monitored using the ninhydrin test and are generally completed in less than 20 minutes. After each coupling step the Fmoc group is removed using a 20% solution of piperidine in DMF.

The phosphorylation reaction is carried out directly on the peptide-resin (0.3 g), which is washed with DMF, DCM and THF, followed by the addition of di-tert butyl-N, N-diethylphosphoramidite (10 eqv/OH) and 1H-tetrazole (30 eqv/OH) in THF (6 mL; 1 hour). After removal of excess reagent, oxidation of the di-tert butyl-phosphate ester is carried out by adding t-butyl hydroperoxide (70%, aqueous, 20 eqv/OH) in DCM (4 mL) to the resin and shaking for 1 hour. The resin is washed with DCM, tert amyl alcohol, and diethylether, and dried. The cleavage is carried out by suspending the resin in a cleavage cocktail (consisted of TFA: phenol: anisole, (96 mL: 2 g: 2 mL respectively)) and shaking for 4 hours. The resin is filtered and washed with dichloromethane. The solvent volume is reduced under vacuum (water aspirator) to approximately 2 mL and the crude product precipitated with the addition of cold ether and finally lyophilized from 0.1% aqueous TFA. Alternatively, the linear peptide is phosphorylated on resin using N, N-diisopropyl-bis(4-chlorobenzyl) phosphoramidate (10 eq) and IH-tetrazole (50 eq) for 1 hour, followed by oxidation with t-butylhydroperoxide (20 eq., 1 hour). The peptide is then cleaved from the resin and purified as described above.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for stimulating activation of gene transcription in a cell, comprising contacting a cell with a modulating agent that inhibits degradation of cytoplasmic β-catenin to thereby stimulate activation of gene transcription in the cell, wherein the agent comprises (i) an internalization moiety and (ii) an amino acid sequence Ser-Tyr-Leu-Asβ-Ser(PO$_4$)-Gly-Ile-His-Ser(PO$_4$)-Gly (SEQ ID NO:1); and wherein the agent contains at most 20 amino acid residues derived from β-catenin.

2. A method according to claim 1, wherein the modulating agent comprises the linear peptide sequence SYLDS(PO$_4$)GIHS(PO$_4$)G (SEQ ID NO:1).

3. A method according to claim 1, wherein the internalization moiety is a peptide internalization sequence.

4. A method according to claim 3, wherein the internalization sequence comprises a sequence selected from the group consisting of RQIKIWFQNRRMKWKK (SEQ ID NO:9), RQIKIWPQNRRNKWKK (SEQ ID NO:10) and YGRKKRRQRRR (SEQ ID NO:4).

5. A method according, to claim 4, wherein the modulating agent has the sequence YGRKKRRQRRRGSYLDS(PO$_4$)GIHS(PO$_4$)G (SEQ ID NO:15).

6. A method according to claim 4, wherein the modulating agent has the sequence SYLDS(PO$_4$)GIHS(PO$_4$)GRQIKIWPQNRRNKWKK (SEQ ID NO:12).

7. A method according to claim 1, wherein the internalization moiety is a liposome.

8. A method according to claim 1, wherein the internalization moiety is an antibody or ligand that specifically binds to a cell surface receptor.

9. A method according to claim 1, wherein the modulating agent is linked to a targeting agent.

10. A method according to claim 1, wherein the modulating agent is present within a pharmaceutical composition comprising a pharmaceutically acceptable carrier.

11. A method according to claim 1, wherein the activation of gene transcription is mediated by a member of the Wnt signaling cascade.

* * * * *

UNITED STATES PATENT AND TRADEMARK OFFICE
CERTIFICATE OF CORRECTION

PATENT NO. : 6,706,685 B1
DATED : March 16, 2004
INVENTOR(S) : Orest W. Blaschuk et al.

It is certified that error appears in the above-identified patent and that said Letters Patent is hereby corrected as shown below:

Title page,
Item [56], References Cited, OTHER PUBLICATIONS,
"Oxford et al." should read as -- Orford et al. --.

Column 23,
Lines 61-62, "Ser-Tyr-Leu-Asβ-Ser($PO_4$)-Gly-Ile-His-Ser($PO_4$)-Gly (SEQ ID NO:1)"
should read -- Ser-Tyr-Leu-Asp-Ser($PO_4$)-Gly-Ile-His-Ser($PO_4$)-Gly (SEQ ID NO:1) --.

Column 24,
Lines 63-64, "YGRKKRRQRRGSYLDS($PO_4$)GIHS($PO_4$)G (SEQ ID NO:15)." should read -- YGRKKRRQRRRGSYLDS($PO_4$)GIHS($PO_4$)G (SEQ ID NO:15). --.

Signed and Sealed this

Twenty-fifth Day of October, 2005

JON W. DUDAS
*Director of the United States Patent and Trademark Office*